(12) United States Patent
Shin et al.

(10) Patent No.: US 9,770,353 B2
(45) Date of Patent: Sep. 26, 2017

(54) COMBINED CAUTERIZATION AND STENT OPERATION DEVICE

(71) Applicant: Taewoong Medical Co. Ltd., Gimpo-si, Gyeonggi-do (KR)

(72) Inventors: Kyung Min Shin, Seoul (KR); Kyung Hoon Shin, Gimpo-si (KR); Dong Un Kim, Gimpo-si (KR)

(73) Assignee: Taewoong Medical Co., Ltd., Gyeonggi-do (KR)

( * ) Notice: Subject to any disclaimer, the term of this patent is extended or adjusted under 35 U.S.C. 154(b) by 288 days.

(21) Appl. No.: 14/401,885

(22) PCT Filed: May 10, 2013

(86) PCT No.: PCT/KR2013/004141
§ 371 (c)(1),
(2) Date: Nov. 18, 2014

(87) PCT Pub. No.: WO2013/172599
PCT Pub. Date: Nov. 21, 2013

(65) Prior Publication Data
US 2015/0133927 A1    May 14, 2015

(30) Foreign Application Priority Data
May 18, 2012 (KR) .................. 10-2012-0053126

(51) Int. Cl.
*A61F 2/962* (2013.01)
*A61B 18/14* (2006.01)
(Continued)

(52) U.S. Cl.
CPC .......... *A61F 2/962* (2013.01); *A61B 18/1206* (2013.01); *A61B 18/1492* (2013.01);
(Continued)

(58) Field of Classification Search
CPC .................. A61B 2018/126; A61B 2018/1497
See application file for complete search history.

(56) References Cited

U.S. PATENT DOCUMENTS 5,178,618 A    1/1993  Kandarpa
5,545,193 A *  8/1996  Fleischman ............ A61N 1/403
                                                      600/373
(Continued)

FOREIGN PATENT DOCUMENTS

CN        1901844 A      1/2007
CN      101448466 A      6/2009
(Continued)

OTHER PUBLICATIONS

Office Action from corresponding EP Patent Application No. 13791710.
(Continued)

*Primary Examiner* — Daniel Fowler
*Assistant Examiner* — Sean W Collins
(74) *Attorney, Agent, or Firm* — Anderson Gorecki LLP

(57) ABSTRACT

A combined cauterization and stent operation device for moving a stent to a lesion of a tubular tissue through a pipe member and performing a stent operation is provided that includes a bipolar electrode for cauterization configured to be disposed at an operation end of the pipe member to cauterize the lesion, and a high frequency generator configured to be connected to the bipolar electrode for cauterization to allow the bipolar electrode for cauterization to radiate a high frequency current.

6 Claims, 12 Drawing Sheets

(51) Int. Cl.
*A61B 18/00* (2006.01)
*A61B 18/12* (2006.01)

(52) U.S. Cl.
CPC ............... *A61B 2018/00345* (2013.01); *A61B 2018/00595* (2013.01); *A61B 2018/126* (2013.01)

(56) References Cited

U.S. PATENT DOCUMENTS

| | | | |
|---|---|---|---|
| 5,749,914 A | 5/1998 | Janssen | |
| 5,921,954 A | 7/1999 | Mohr, Jr. et al. | |
| 6,014,589 A * | 1/2000 | Farley | A61B 18/1492 606/191 |
| 6,030,382 A * | 2/2000 | Fleischman | A61B 5/0422 374/E1.005 |
| 6,139,536 A | 10/2000 | Mikus et al. | |
| 7,209,783 B2 | 4/2007 | Fellows et al. | |
| 2003/0018362 A1 * | 1/2003 | Fellows | A61B 18/1492 607/5 |
| 2004/0143256 A1 * | 7/2004 | Bednarek | A61B 18/1492 606/41 |
| 2006/0161246 A1 | 7/2006 | Rhim et al. | |
| 2006/0276873 A1 | 12/2006 | Sato | |
| 2007/0149963 A1 * | 6/2007 | Matsukuma | A61B 18/04 606/28 |
| 2009/0143777 A1 * | 6/2009 | Pacey | A61B 18/1492 606/27 |
| 2010/0191151 A1 * | 7/2010 | Kwak | A61B 18/1492 600/585 |

FOREIGN PATENT DOCUMENTS

| | | |
|---|---|---|
| CN | 102038565 | 5/2011 |
| JP | H09140807 | 6/1997 |
| JP | 2005/125102 | 5/2005 |

OTHER PUBLICATIONS

Office Action from corresponding CN Patent Application No. 201380026011.0.
International Search Report from corresponding PCT application PCT/KR2013/004141.
Office Action from corresponding JP Patent Application No. 2015-512571 dated Oct. 9, 2015 (3 pages).

* cited by examiner

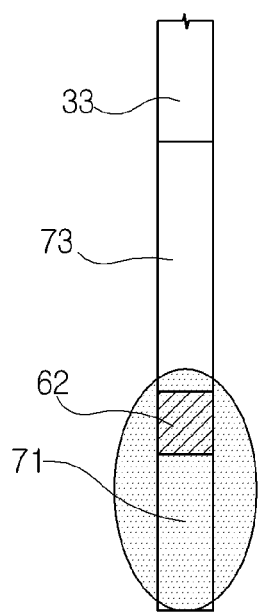

COMBINED CAUTERIZATION AND STENT OPERATION DEVICE

TECHNICAL FIELD

The present invention relates to a combined cauterization and stent operation device, and more particularly, to a combined cauterization and stent operation device capable of reducing an occurrence risk of re-stricture at a lesion after a stent is operated, by cauterizing the lesion before or after the stent is operated while performing an operation of the stent on the lesion occurring in a body organ, in particular, a tubular tissue such as a blood vessel.

BACKGROUND ART

Generally, when a stricture, and the like occurs in a tubular tissue of a body such as a blood vessel, hematogenous disorder is caused or the tubular tissue is occluded, and thus in the worst case, it is likely to lead to the death In this case, the related art removes a lesion by a surgical operation and replaces a removed portion with an artificial construction and therefore has a problem in that a big scar remains in surgery areas, convalescence is required for a considerable period of time, and the like.

Recently, therefore, a non-surgical treatment method for performing a stent operation has been proposed. An example of the stent operation apparatus for performing a stent operation may include an apparatus 201 illustrated in FIGS. 1 and 2.

As illustrated, the stent operation apparatus 201 includes a fixed pipe 231 disposed therein and a moving pipe 233 inserted into an outer side thereof, and is configured to move a stent S charged between a front end of the fixed pipe 231 and the moving pipe 233.

To this end, as illustrated, the fixed pipe 231 has the front end provided with a streamlined guide tip 243, in which a front end just behind the guide tip 243 is provided with a stent sheet 241 for charging the stent S while the stent sheet 241 being diameter-reduced and a rear end thereof is provided with a fixed handle (not illustrated) for gripping. Further, as illustrated in FIG. 1, the moving pipe 233 is inserted to slidably move on the fixed pipe 231 until an inner portion of the guide tip 234 is sealed while contacting the rear end of the guide tip 243 and is formed in a hollow pipe body and a rear end thereof is attached with a moving handle (not illustrated).

Therefore, when the stent operation apparatus 201 according to the related art intends to perform the stent S operation, first, as illustrated in FIG. 1, the moving pipe 233 pushes the operation apparatus 201 into a tubular tissue such as a blood vessel V in an arrow direction in a sealing state in which the moving pipe 233 adheres up to a projection 247 of the fixed pipe 231 so that the stent S charged therein is accurately positioned at a lesion.

Next, when the moving pipe 233 is pulled in an arrow direction of FIG. 2 to relatively move backward with respect to the fixed pipe 231, the stent S charged in the stent sheet 241 is extended by elasticity of the stent S itself while the stent sheet 241 is opened, and at the same time, is separated from the sheet 241 to press a lesion to the outside and extend a lumen of the blood vessel V blocked due to a lesion, thereby ending the stent S operation.

However, as illustrated in FIG. 2, when the stent operation apparatus 201 according to the related art as described above operates the stent S, a tissue of a lesion pushed to the outside by the stent S after a predetermined time elapses grows between meshes of the stent S to cause a re-stricture at the lesion.

To solve the above problem, a pre-operation cauterizing and necrotizing a lesion using a cauterization electrode apparatus is performed, and then the stent S operation is performed to prevent the above re-stricture. However, for this purpose, since a pre-operation of charging and removing an electrode needle of the cauterization into a blood vessel needs to be performed, efficiency of the operation such as an increase in a burden to a patient or an operator and an increase in operation cost due to the pre-operation may be reduced.

DISCLOSURE

Technical Problem

The present invention proposes to solve the foregoing problem, and an object of the present invention is to remove inefficiency of an operation due to repetitive performance of a pre-operation and a main operation while preventing a re-stricture from occurring at a lesion after a stent operation is performed, by allowing a single apparatus to perform the pre-operation cauterizing a lesion prior to performing the stent operation and the main operation performing the stent operation on a cauterized and necrotized lesion.

Technical Solution

To achieve the above object, according to the present invention, there is provided a combined cauterization and stent operation device moving a stent to a lesion of a tubular tissue through a plurality of pipe members and performing a stent operation, including: a bipolar electrode for cauterization configured to be disposed at an operation end of the pipe member to cauterize the lesion; and a high frequency generator configured to be connected to the bipolar electrode for cauterization to allow the bipolar electrode for cauterization radiate a high frequency current.

The pipe member may include: a fixed pipe configured to have one end attached with a fixed handle for gripping and the other end provided with a stent sheet for seating a stent; and at least one moving pipe configured to have one end attached with a moving handle for gripping and be movably inserted longitudinally into an outer peripheral surface of the fixed pipe to charge the stent in the fixed pipe in a compressed state in the stent sheet, in which the bipolar electrode for cauterization is disposed at one side of an operation end corresponding to the fixed or moving handle of the fixed pipe or the moving pipe.

The moving pipe may further include a temperature sensor installed at a portion where the cauterization is performed by the bipolar electrode for cauterization to monitor a temperature of a tissue before cauterization, during cauterization, or after cauterization.

The bipolar electrode for cauterization may be configured of at least one pair of active electrode and passive electrode spaced apart from each other with at least one insulating gap.

The pair of active electrode and passive electrode may have a symmetrical structure, having the same surface area.

The pair of active electrode and passive electrode may have an asymmetrical structure, having different surface areas.

The outer peripheral surface of the fixed pipe or the moving pipe corresponding to the insulating gap may be provided with an insulating part.

The bipolar electrode for cauterization may include: an active electrode configured to be wound around one side of the outer peripheral surface of the fixed pipe or the moving pipe in a spiral form in plural times; and a passive electrode configured to be wound around one side of the outer peripheral surface of the fixed pipe or the moving pipe through the active electrode in plural times.

The active electrode and the passive electrode may be wound on an outer peripheral surface of the body at a constant alternating gap therebetween.

The active electrode body or the passive electrode body may each include continuously overlapping concentration parts without any one thereof alternating with the other one electrode and the concentration part may be wound around the outer peripheral surface of the body at a denser gap than the alternating gap of the electrode bodies or gapless.

The insulating gap may be formed between the concentration part of the any one electrode and the concentration part of the other electrode.

The outer peripheral surface of the body corresponding to the insulating gap may be provided with an insulating part.

In the bipolar electrode for cauterization, a lead wire continued to the high frequency generator through the moving handle may be formed as extending wires of the active electrode and the passive electrode and the lead wire may be finished so as not to be exposed to the outside by a coating part coated on the moving pipe.

DESCRIPTION OF DRAWINGS

FIGS. 5A to 5C are diagrams illustrating a modified example of the stent operation apparatus illustrated in FIG. 3.

DETAILED DESCRIPTION OF EMBODIMENTS

Hereinafter, a combined cauterization and stent operation device according to an exemplary embodiment of the present invention will be described with reference to the accompanying drawings.

Figure 1:
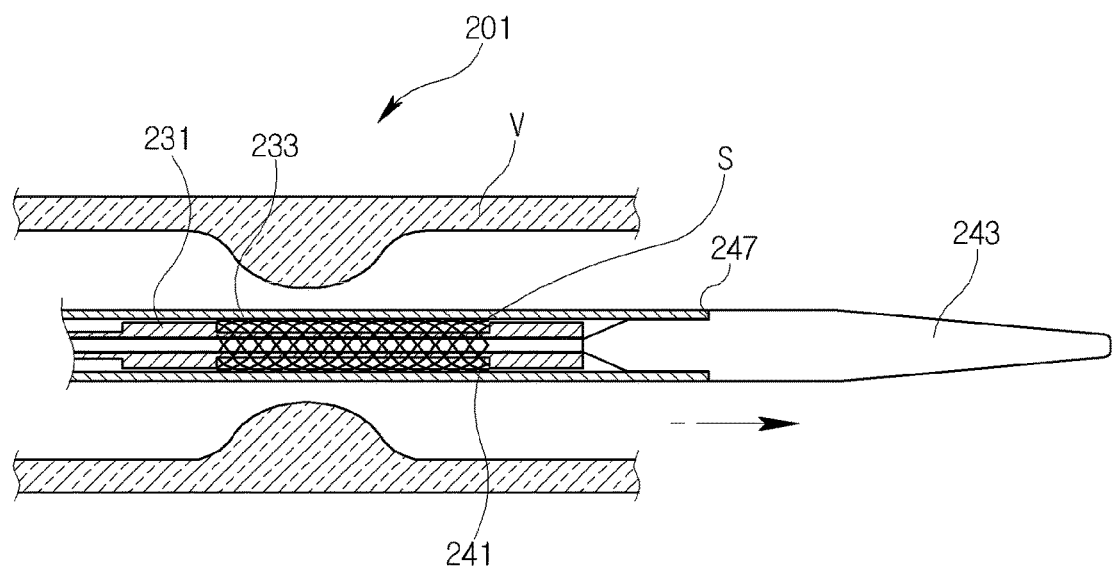
FIG. 1 is a front cross-sectional view illustrating a stent operation apparatus according to the related art in a state before a stent operation is performed.
Figure 2:
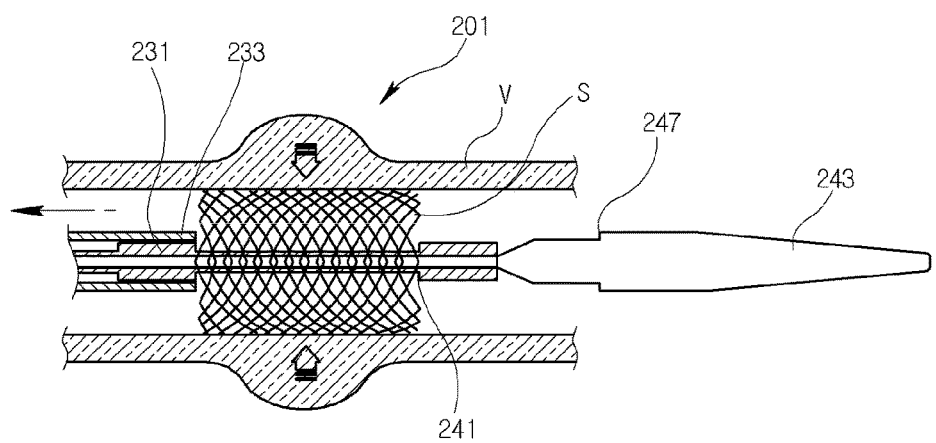
FIG. 2 is a front cross-sectional view illustrating the stent operation apparatus in a state after the stent operation is performed.
Figure 3:
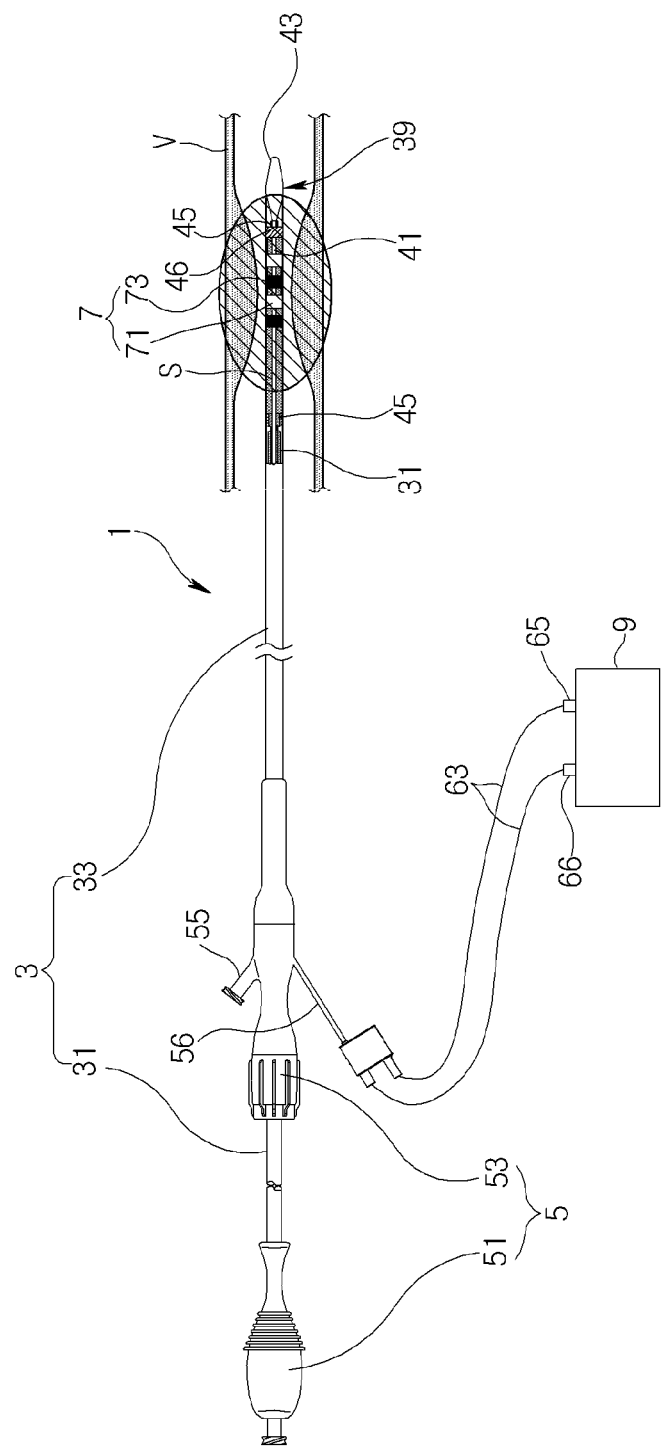
FIG. 3 is a front cross-sectional view illustrating a stent operation apparatus according to a first embodiment of the present invention in a state before a stent operation is performed.

A stent operation apparatus according to an embodiment of the present invention moves a stent S to a lesion of a tubular tissue such as a blood vessel V and performs the stent S operation and as illustrated in FIG. 3, the stent operation apparatus 1 largely includes a plurality of pipe members 3 and a handle 5, in particular, a bipolar electrode 7 for cauterization and a high frequency generator 9.

First, the pipe member 3 which is a hollow or solid tubular member forming a body of the stent operation apparatus 1 is confirmed of a plurality of pipes 31 and 33 to have the stent S mounted therein and move the stent S into a tubular tissue such as a blood vessel V. The shape, number, or the like of pipes 31 and 33 may be variously changed depending on a usage or a size of the operation apparatus 1, but according to the embodiment, as illustrated in FIG. 3, the pipe member 3 is configured of a fixed pipe 31 and a moving pipe 33.

Figure 4:
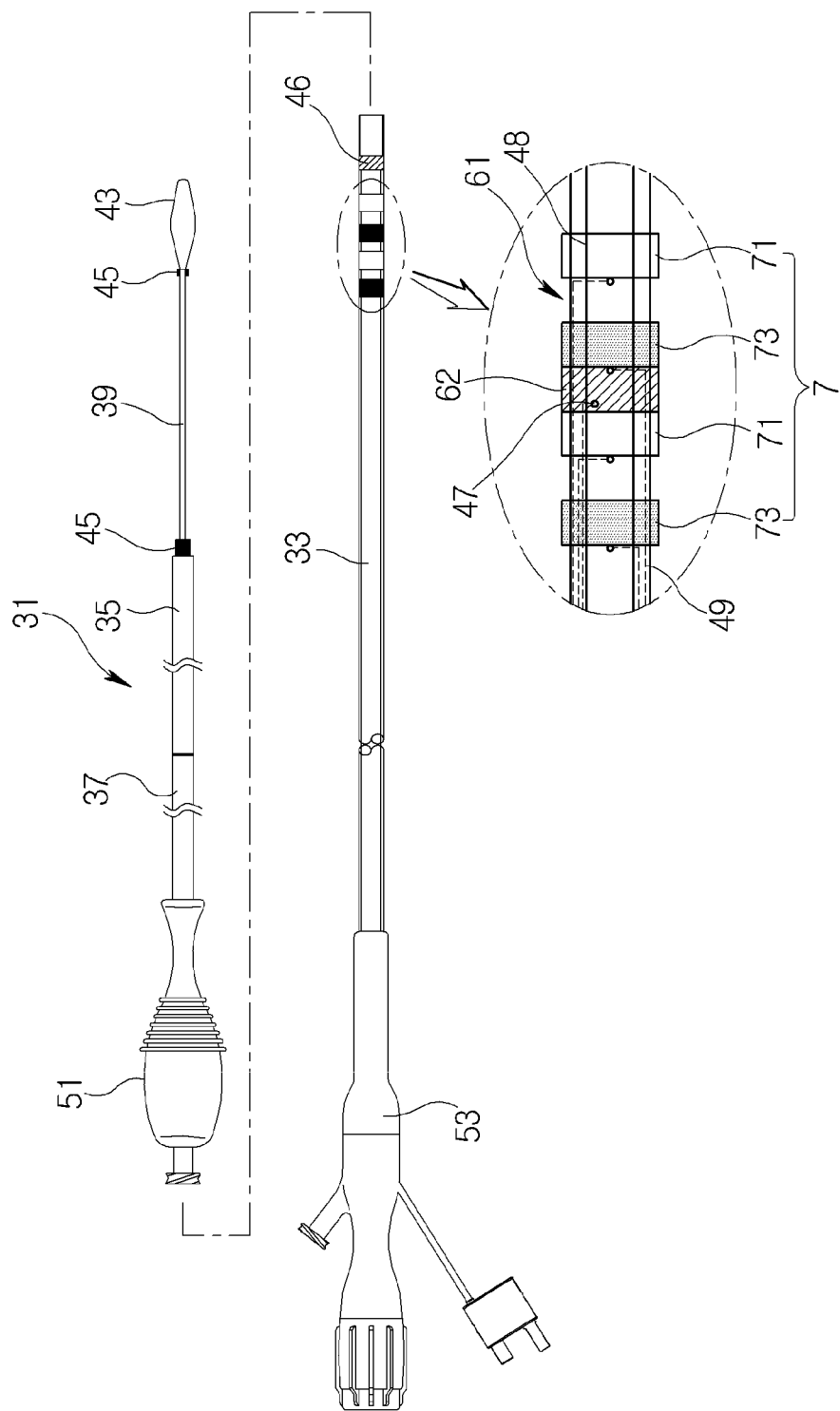
FIG. 4 is an exploded view of FIG. 3.

In this configuration, the fixed pipe 31 is a basic part of the stent operation apparatus 1 and as illustrated in FIG. 4, is configured of three parts, that is, a pipe body 35 made of a flexible material such as PC to move along a blood vessel V, a pusher 37 coupled with a rear end of the pipe body 35 and made of a metal material such as SUS having high rigidity, and a stent wire 39 coupled with a front end of the pipe body 35, that is, an operation end and having a front end provided with a streamlined guide tip 43. In this case, the pusher 37 has a rear end attached with a fixed handle 51 for gripping at the time of operation and when the moving handle 53 is pulled backward to extract the moving handle 53 without warpage, is configured to relatively move without warpage so as to enter the moving handle 53. Further, as illustrated in FIG. 3, the stent wire 39 has a reduced diameter to form a stent sheet 41 to secure a charging space of the stent S in the moving pipe 33. In this case, in the stent wire 39, both ends of a front and a rear the stent sheet 41 are provided with X-ray display units 45 at so as to check a charging position of the stent S at the time of an operation.

Meanwhile, the fixed pipe 31 is not illustrated in detail in the drawing, but the bipolar electrode 7 may be formed at a front end, that is, one side of the operation end, for example, on an outer peripheral surface of the stent wire 39.

Figure 6:
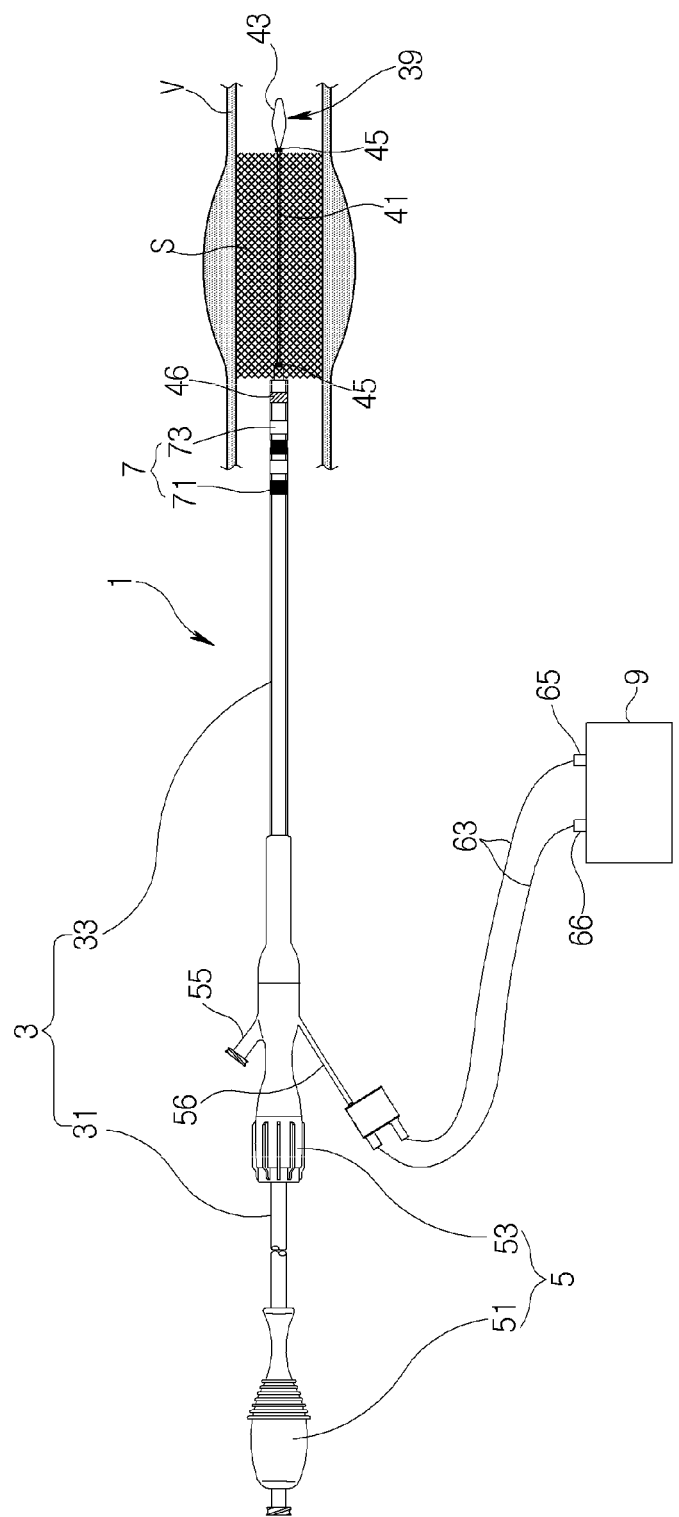
FIG. 6 is a front cross-sectional view illustrating the stent operation apparatus of FIG. 3 in a state after the stent operation is performed.

The moving pipe 33 is a means for opening the stent S charted in the fixed pipe 31 at a desired position and as can be appreciated in FIGS. 3 and 6, the moving pipe 33 is seated in the stent sheet 41 to open the stent S charged in a compressed state in the fixed pipe 31 so as to operate a lesion and is relatively movably inserted longitudinally into an outer peripheral surface of the fixed pipe 31. Therefore, as illustrated in FIGS. 3 and 4, the moving pipe 33 has a hollow pipe shape and has a rear end attached with a moving handle 53 for gripping at the time of an operation and a front end wound with an X-ray display unit 45 for position confirmation. Further, the moving pipe 33 has a rear end provided with the bipolar electrode 7 for cauterization to be described below and a temperature sensor 47 for confirming a temperature of the bipolar electrode 7 and is finished to have a double structure in which a wiring pipe 48 is inserted into the moving pipe 33 so as not to hinder a relative movement of lead wires 49 connected to the bipolar electrode 7 and the temperature sensor 47 with respect to the fixed pipe 31.

In this case, the temperature sensor 47 may be positioned at the electrode 7 portion of the cauterized moving pipe 33 to monitor a temperature of a tissue before cauterization, during cauterization, or after cauterization. A temperature value measured during the cauterization is information on how much the cauterization is performed. Based on the information, it is possible prevent the phenomenon that a heat generation range is beyond a lesion to cauterize and damage normal tissues, the phenomenon that the heat generation range does not reach the lesion to hinder a complete cauterization of the lesion, and the like.

Meanwhile, as described above, the handle 5 which is a means for gripping the pipe member 3 when the stent operation apparatus 1 performs the stent S operation includes a fixed handle 51 attached to the rear end of the fixed pipe 31 and a moving handle 53 attached to the rear end of the moving pipe 33 as illustrated in FIGS. 3 and 4. In this case, the fixed handle 51 is used at the time of gripping to push or extract the overall operation apparatus 1 into or from the blood vessel V and the moving handle 53 is used at the time of performing the stent S operation on the lesion by pulling the moving pipe 33 as illustrated in FIG. 6. In particular, as illustrated in FIG. 3, the moving handle 53 has one side provided with a supply and drain pipe which supplies washing water, and the like to the blood vessel V and extracts a blood, and the like introduced into the pipe member 3 and the other side provided with an inlet pipe 56 for extracting the lead wire continued to the bipolar electrode 7 and the temperature sensor 47 outside the pipe member 3.

Meanwhile, the high frequency generator 9 which is an apparatus generating a high frequency alternating current is widely used for a general electrical operation and as described to be below, is configured to have a positive terminal and a negative terminal selectively connected to the active electrode body 71 or the passive electrode body 73 of the bipolar electrode 7 so as to supply the high frequency alternating current to the bipolar electrode 7 for cauterization.

Further, the bipolar electrode 7 for cauterization is an electrical conductor cauterizing a lesion before or after the stent S operation is performed on the lesion such as a blood vessel V and as illustrated in FIGS. 3 and 4, is configured to be wound around the pipe member 3, that is, in the present embodiment, the operation end of the front end of the moving pipe 33 facing the moving handle 53 in a band shape and is configured of at least one pair of active electrode 71 and passive electrode 73 spaced apart from each other at at least one insulating gap 61. The active electrode 71 and the passive electrode 73 each are electrically connected to active and passive terminals 65 and 66 of the high frequency generator 9 through an electrode wire 63 connected to the lead wire 49 and configured to radiate high frequency energy between counter electrodes 71 and 73 which are alternately arranged longitudinally to form a pair.

In this case, even in the case in which the insulating part 62 is attached by being wound around the outer peripheral surface of the moving pipe 33 corresponding to the insulating gap 61 between the active electrode 71 and the passive electrode 73, the high frequency energy radiation efficiency from the active electrode 71 and the passive electrode 73 may be increased and as the insulating part 62, a flexible material such as Teflon and synthetic resin may be preferably used.

Figure 5A:
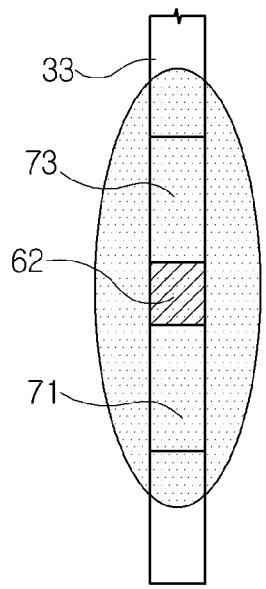
Figure 5B:
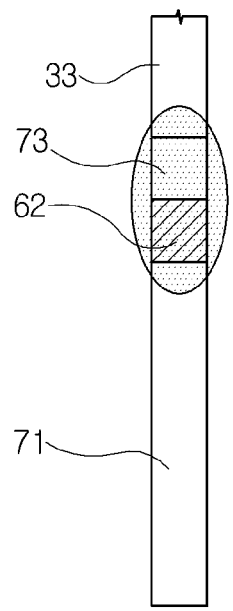

Further, the active electrode 71 and the passive electrode 73 may be in various forms and sizes and as illustrated in FIGS. 4 and 5A, when the pair of corresponding active electrode 71 and passive electrode 73 has a symmetrical structure having the same surface area, as represented by an oval, the cauterization is performed in all the electrodes 71 and 73 but as illustrated in FIGS. 5B and 5C, when the active electrode 71 and the passive electrode 73 are asymmetrical due to different surface areas, the cauterization is performed only by any one of the active electrode 71 or the passive electrode 73 having a relatively smaller surface area. Therefore, the surface area ratio of the electrodes 71 and 73 are appropriately selected, and thus as illustrated in FIG. 5B, the cauterization is performed by the passive electrode 73, as illustrated in FIG. 5C, the cauterization is performed by the active electrode 71, or the like, such that a range, a form, a speed, and the like of cauterization may be easily controlled.

Figure 7:
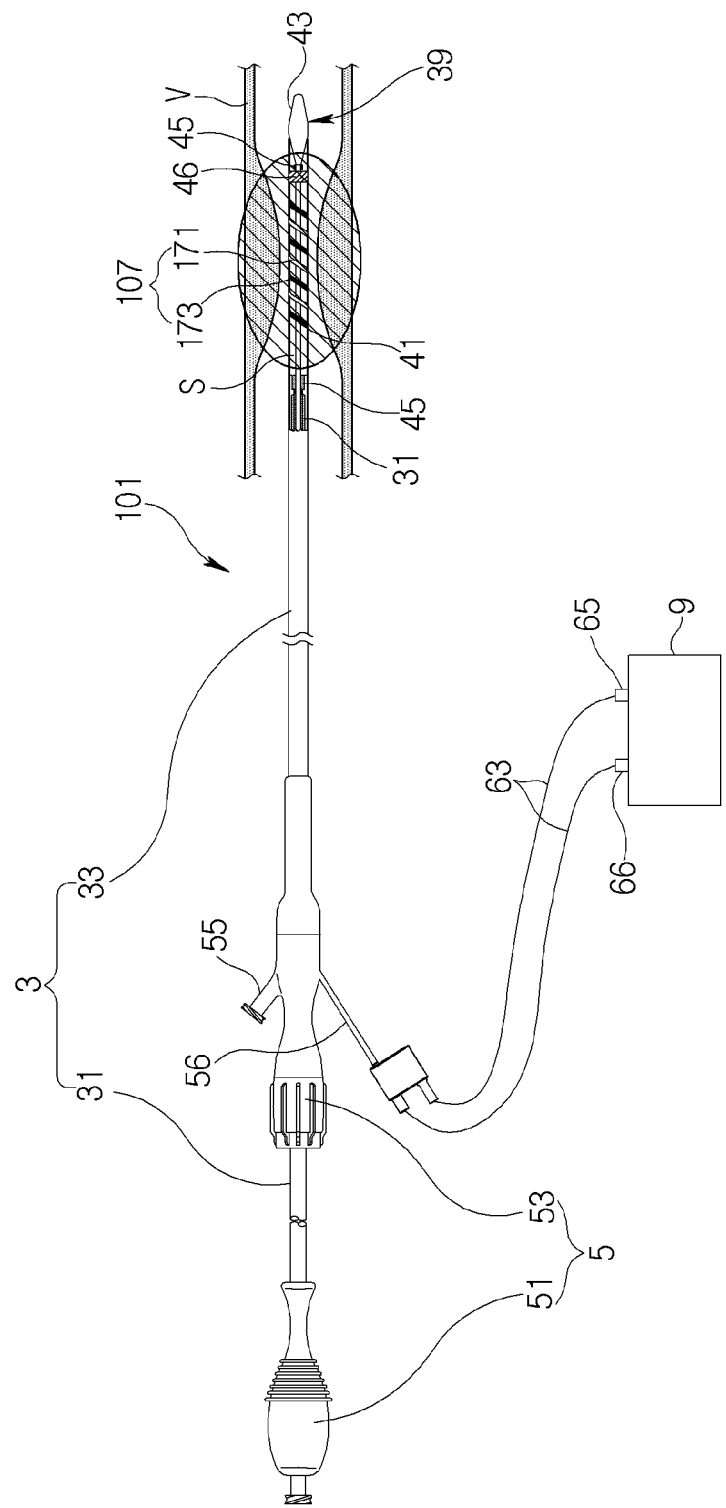
FIG. 7 is a front cross-sectional view illustrating a stent operation apparatus according to a second embodiment of the present invention in a state before a stent operation is performed.

Likewise the stent operation apparatus according to the first embodiment illustrated in FIG. 3, a stent 101 provided with a cauterization system according to another embodiment of the present invention illustrated in FIG. 7 is configured of the plurality of pipe members 3 and the handle 5 and is configured to include a bipolar electrode 107 for cauterization and the high frequency generator 9.

Here, all the pipe member 3, the handle 5, and the high frequency generator 9 are the same as those of the first embodiment described above and therefore the description thereof will be omitted.

However, unlike the electrode 7 according to the first embodiment, the bipolar electrode 107 for cauterization is configured of an active electrode 171 and a passive electrode 173 which are alternately wound around the outer peripheral surface of the moving pipe 33, in which each electrode 171 and 173 is wound around the outer peripheral surface of the moving pipe 33 to be inclined backward in a spiral direction from the front end. In this case, the two electrodes 171 and 173 are wound at the same lead angle in parallel at least twice or more.

Figure 8:
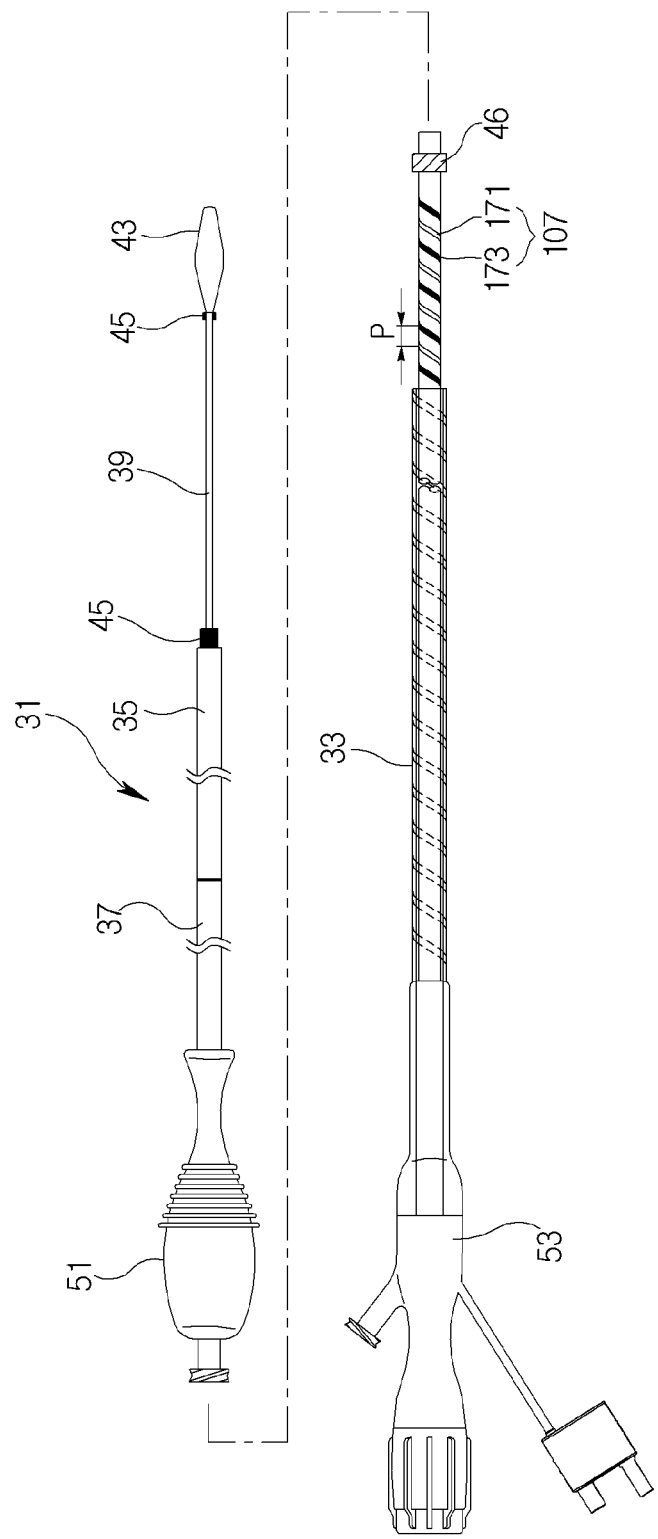
FIG. 8 is an exploded view of FIG. 7.

Among those, the active electrode 171 has the other end connected to an active terminal 65 of the high frequency generator 5 through the electrode line 13 and the passive electrode body 173 has the other end connected to a passive terminal 66 of the high frequency generator 5 through the electrode wire 63. In this case, the active terminal 65 or the passive terminal 66 may be a positive pole or a negative pole according to selection. In particular, as illustrated in FIGS. 7 and 8, in the bipolar electrode 107 for cauterization, since the passive electrode 173 is also wound to be inclined through the active electrode 171 wound in a spiral direction, the active electrode 171 and the passive electrode 173 keep a gap from each other, and thus heat generation starts around an intermediate point of a pitch P of each electrode 171 and 173 at the time of radiating the high frequency. In this case, since the pitch P is shorter than a diameter of the moving pipe 33, the heat generation range, that is, the range in which the cauterization is performed has a cylindrical shape enclosing the moving pipe 33 and more preferably, when the pitch P between the electrodes 171 and 173 is constant as illustrated, that is, when an alternating gap between the electrodes 171 and 173 is constant, the heat generation range has a cylindrical shape of which a longitudinal section is a rectangle.

Figure 9:
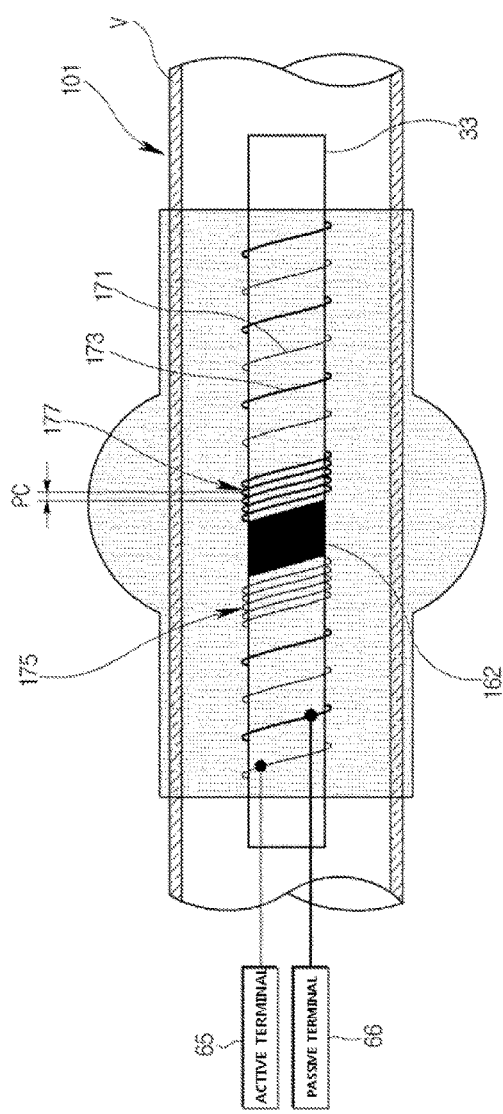
FIGS. 9 and 10 are diagrams illustrating a modified example of the stent operation apparatus illustrated in FIG. 7.
Figure 10:
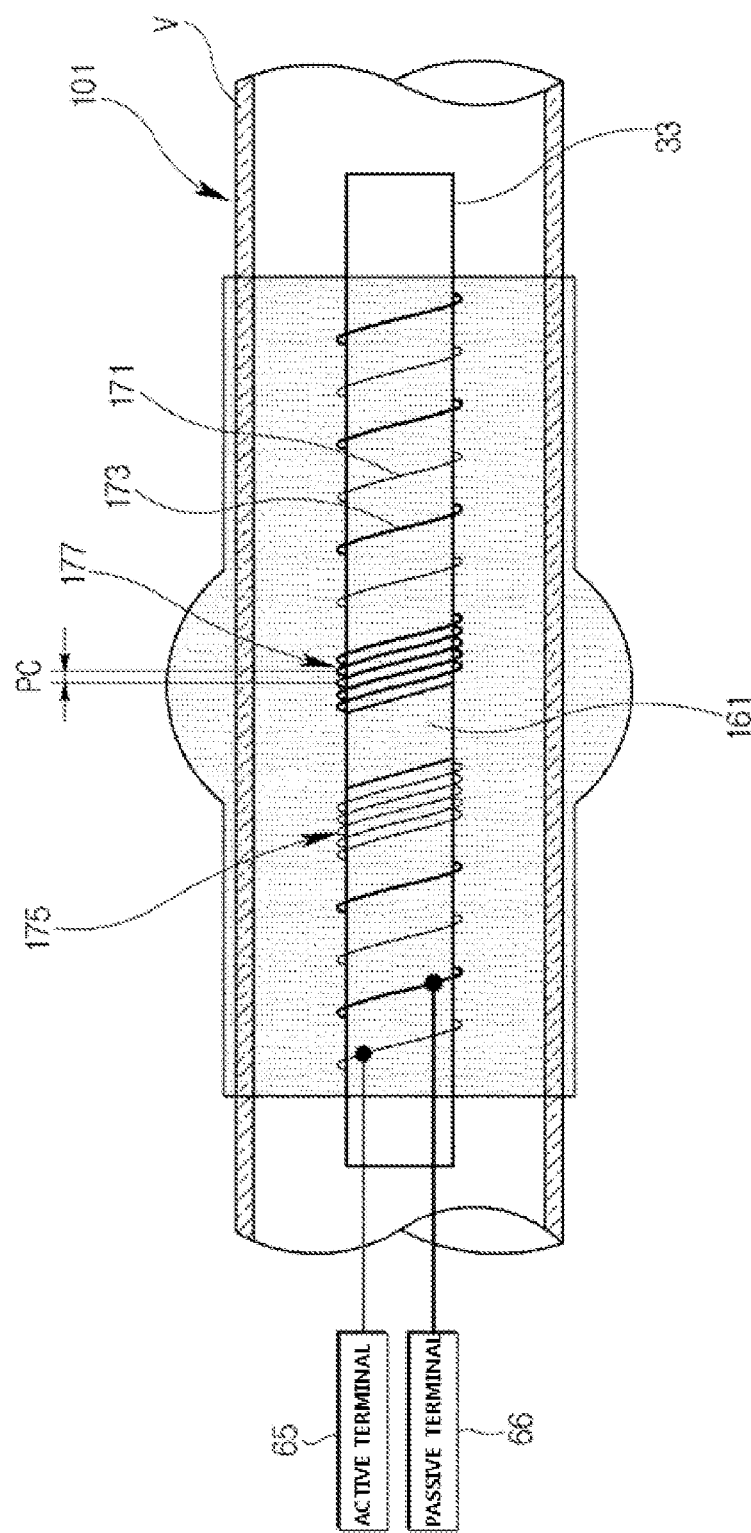

Further, in the bipolar electrode 107 for cauterization according to another embodiment of the present invention, as illustrated in FIGS. 9 and 10, more than one concentration part 175 and 177 may be formed while one-to-one matching the active electrode 171 and the passive electrode 173. As illustrated, the concentration parts 175 and 177 of each of the active electrode 171 and the passive electrode 173 are formed at a position at which they match the passive electrode 173 or the active electrode 171, and therefore, unlike the other portion of the electrodes 171 and 173, one electrode is continuously wound without alternating with the other electrode.

In this case, in order to increase an emission density of high frequency energy, as illustrated in FIGS. 9 and 10, each of the concentration parts 175 and 177 is wound around the outer peripheral surface of the moving pipe 33 at an interval of the pitch P of the electrodes 171 and 173 which is denser than that of the pitch P of the other portion of the electrodes 171 and 173, preferably, without the interval of the pitch, that is, gapless.

As described above, each of the concentration parts 175 and 177 may not be considered as one winding body since the pitch P of a winding is short or is not present, such that as illustrated in FIG. 9, as another embodiment, an insulating gap 161 is secured between the corresponding concentration parts 175 and 177, thereby increasing the high frequency energy radiation efficiency.

As another embodiment, when an insulating part 162 is formed on the outer peripheral surface of the moving pipe of the insulating gap between the corresponding concentration parts 175 and 177 as illustrated in FIG. 10, even though the insulating gap 161 between the corresponding concentration parts 175 and 177 is not sufficiently secured as illustrated in FIG. 9, the insulating part 162 may keep insulating performance, thereby increasing the high frequency energy radiation efficiency.

Figure 11:
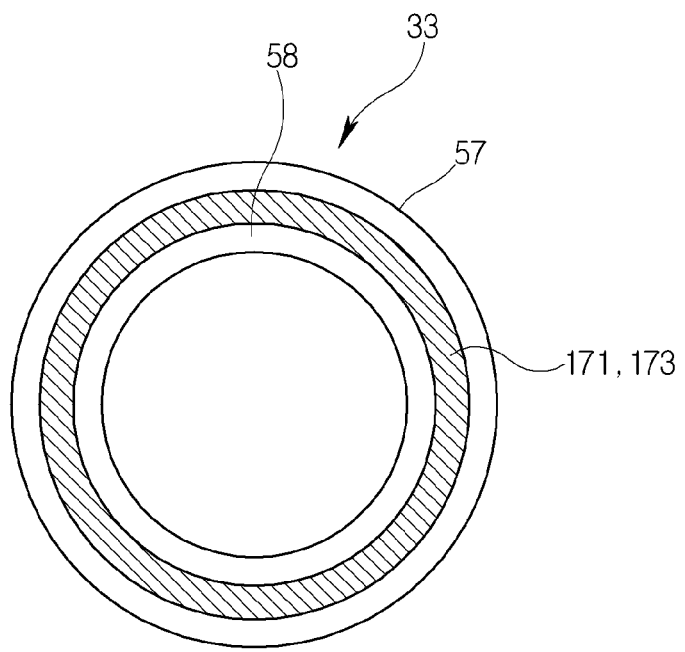
FIG. 11 is a transverse cross-sectional view of a moving pipe illustrated in FIG. 7.

Meanwhile, the active electrode 171 and the passive electrode 173 are connected to the electrode wire 63 continued to the high frequency generator 9 through the moving handle 53 integrally formed at the rear end of the moving pipe 33 and unlike the first embodiment in which the lead wire 49 is extracted from the moving handle 53 through a separate wiring pipe 48, the electrodes 171 and 173 are used as the lead wire 49 as they are. As illustrated in FIG. 11, the moving pipe 33 is configured of an outer cover part 57 and an inner cover part 58 and the electrodes 171 and 173 alternately wound around an outer peripheral surface of the inner cover part 58 extends to the moving handle 53 as it is to be coated with the outer cover part 57, and thus the front end used as the electrode is exposed to the outside and the rest portion used as the lead wire 49 is finished without being exposed to the outside by the outer cover part 57.

Hereinafter, an action of the stent 1 provided with a cauterization system according to the present invention configured as described above will be described.

When the stent 1 provided with a cauterization system according to the first embodiment of the present invention performs the stent S operation, as illustrated in FIG. 3, first, the operation apparatus 1 is positioned at the lesion such as a blood vessel V. In this case, the bipolar electrode 7 for cauterization is accurately positioned at a center of the lesion using the X-ray display unit 46 attached to the front end of the moving pipe 33.

Next, when the high frequency generator 9 is operated to radiate the high frequency current through the active electrode 71 and the passive electrode 73, ions of lesion tissue generate vibration by energy generated in an energy radiation zone represented by an oval in FIG. 3 to generate friction heat, such that the cauterization is performed by the friction heat.

Then, when the moving pipe 33 relatively moves while the position of the fixed pipe 31 is fixed, as illustrated in FIG. 6, the stent S charged in the stent sheet 41 of the front end of the fixed pipe 31 is extended by elasticity of the stent S itself to adhere to the blood vessel V. In this case, the stent S operation position may also be confirmed by the X-ray display units of both ends of the stent sheet 41. By doing so, the stent S performing the operation may push a lesion to secure a diameter of a lumen of the blood vessel V.

Meanwhile, likewise the case in which stent operation apparatus 101 according to the second embodiment performs the stent S operation, as illustrated in FIG. 7, first, the operation apparatus 10 is accurately positioned at the lesion such as the blood vessel V using the X-ray display unit 46.

Next, when the high frequency generator 9 is operated, the high frequency alternating current is radiated between the active electrode 71 and the passive electrode 73. In this case, as illustrated in FIG. 7, the active electrode 71 and the passive electrode 73 radiate the high frequency energy between adjacent electrodes to the interval of the pitch P and an electrode to form a high frequency energy radiation zone in a general cylindrical shape and the lesion is cauterized by the heat generated from the radiation zone. In this case, the lesion of the tubular organ such as a blood vessel V may be effectively cauterized at a minimum thickness by the cylindrical radiation zone following the form of the lesion, that is, without the damage of other adjacent tissues.

Further, according to another embodiment of the present invention, as illustrated in FIGS. 9 and 10, the heat generation range in a cylindrical shape, that is, the heat generation range having a longitudinal section in a rectangular shape is formed by the electrodes 171 and 173 and in addition, the heat generation range in an oval shape based on the insulating gap 161 or the insulating part 162, that is, the heat generation range having a longitudinal section in an oval shape is formed at least one depending on the number of a pair of corresponding concentration parts 175 and 177. Therefore, even in the case of the lesion having a portion which is widely distributed out of the tubular shape, that is, even in the case in which a lesion widely distributed in a radius direction of a blood vessel occurs at a specific position while being distributed as a whole in the tubular tissue such as a blood vessel in a longitudinal direction, the concentration parts 175 and 177 match the lesion widely distributed in a radius direction, thereby effectively performing the cauterization.

Figure 12:
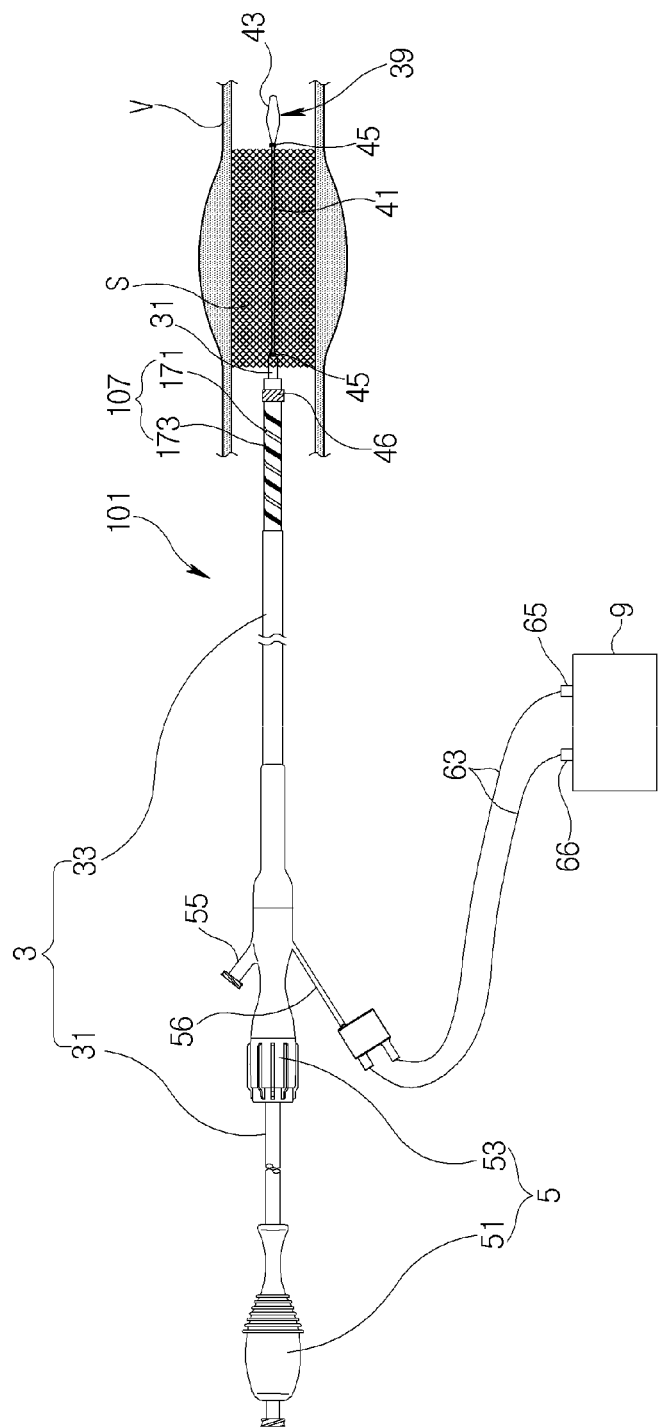
FIG. 12 is a front cross-sectional view illustrating a stent operation apparatus according to a second embodiment of the present invention in a state after a stent operation is performed.

Next, likewise the first embodiment, the moving pipe 33 relatively moves while the position of the fixed pipe 31 is fixed, and thus as illustrated in FIG. 12, the stent S charged in the stent sheet 41 is extended by elasticity of the stent S itself to adhere to the cauterized lesion, thereby ending the stent S operation.

INDUSTRIAL APPLICABILITY

According to the combined cauterization and stent operation device according to the present invention, the lesion may be cauterized and necrotized by the bipolar electrode of a tip portion of a moving pipe charged with the stent before or after the stent is operated on the lesion, thereby effectively preventing a re-stricture from occurring at the lesion operated by the stent.

In addition, the single stent operation apparatus may perform the stent operation and the cauterization of the operation portion at a time and therefore there is no need to overlappingly perform the insertion operation of the stent operation apparatus and the insertion operation of the cauterization operation, thereby more improving the operation efficiency such as the reduction in the burden to both of the patient to be operated and the operation performing the operation, the reduction in the operation cost, and the like.

The invention claimed is:
1. A combined cauterization and stent operation device for moving a stent to a lesion of a tubular tissue through a pipe member and performing a stent operation, comprising:
 a bipolar electrode for cauterization configured to be disposed at an operation end of the pipe member to cauterize the lesion; and a high frequency generator configured to be connected to the bipolar electrode for cauterization to allow the bipolar electrode for cauterization to radiate a high frequency current;

wherein the pipe member includes:

a fixed pipe configured to have one end attached with a fixed handle for gripping and the other end provided with a stent sheet for seating a stent; and at least one moving pipe configured to have one end attached with a moving handle for gripping and to be movably inserted longitudinally into an outer peripheral surface of the fixed pipe to charge the stent in the fixed pipe in a compressed state in the stent sheet, in which the bipolar electrode for cauterization is disposed at one side of an operation end corresponding to the fixed or moving handle of the fixed pipe or the moving pipe;

wherein the bipolar electrode for cauterization includes:

an active electrode configured to be wound around one side of the outer peripheral surface of the fixed pipe or the moving pipe in a spiral form several times; and a passive electrode configured to be wound around one side of the outer peripheral surface of the fixed pipe or the moving pipe alternatively with the active electrode several times;

wherein the active electrode and the passive electrode are wound on the outer peripheral surface of the fixed pipe or the moving pipe at a constant alternating gap therebetween; and wherein the active electrode or the passive electrode each include at least one continuously overlapping concentration parts without any one thereof alternating with the other one electrode and the concentration parts are wound around the outer peripheral surface of the fixed pipe or the moving pipe at a constant interval having a denser gap than the alternating gap or gapless.

2. The combined cauterization and stent operation device of claim 1, wherein the moving pipe further includes a temperature sensor installed at a portion where the cauterization is performed by the bipolar electrode for cauterization to monitor a temperature of a tissue before cauterization, during cauterization, or after cauterization.

3. The combined cauterization and stent operation device of claim 1, wherein the outer peripheral surface of the fixed pipe or the moving pipe corresponding to the alternating gap is provided with an insulating part.

4. The combined cauterization and stent operation device of claim 1, wherein an insulating gap is formed between the concentration part of the any one electrode and the concentration part of the other electrode.

5. The combined cauterization and stent operation device of claim 4, wherein the outer peripheral surface of the fixed pipe or the moving pipe corresponding to the insulating gap is provided with an insulating part.

6. The combined cauterization and stent operation device of claim 1, wherein in the bipolar electrode for cauterization, a lead wire connected to the high frequency generator through the moving handle is formed as extending wires of the active electrode and the passive electrode and the lead wire is finished so as not to be exposed to the outside by a coating part coated on the moving pipe.

* * * * *